(12) United States Patent
Fukuchi

(10) Patent No.: US 6,337,345 B1
(45) Date of Patent: Jan. 8, 2002

(54) INSECTICIDAL OR MITICIDAL COMBINATIONS CONTAINING CHLORFENAPYR

(75) Inventor: Toshiki Fukuchi, Yokohama (JP)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/308,848

(22) PCT Filed: Nov. 25, 1997

(86) PCT No.: PCT/JP97/04274

§ 371 Date: May 24, 1999

§ 102(e) Date: May 24, 1999

(87) PCT Pub. No.: WO98/23154

PCT Pub. Date: Jun. 4, 1998

(30) Foreign Application Priority Data

Nov. 25, 1996 (JP) ............................................. 8-313571

(51) Int. Cl.[7] ........................ A01N 43/36; A01N 53/00; A01N 43/54; A01N 43/00
(52) U.S. Cl. ........................ 514/427; 514/428; 514/183; 514/256
(58) Field of Search ................................ 514/427, 428, 514/256, 183

(56) References Cited

U.S. PATENT DOCUMENTS 4,705,801 A * 11/1987 Martin et al. ................ 514/423
4,798,901 A * 1/1989 Tessier et al. ............... 548/562
5,010,098 A * 4/1991 Brown et al. ................ 514/426
5,965,602 A * 10/1999 Takada et al. .............. 514/427

FOREIGN PATENT DOCUMENTS

| EP | 0 492 125 A1 | 7/1992 |
| EP | 0492171 | * 7/1992 |
| JP | O 771 526 A2 | 5/1997 |

OTHER PUBLICATIONS

J.R. Whitehead et al: "Performance of Pirate, insecticide–miticide, against cotton–pests in the mid–south in 1992" Porceedings Beltwide Cotton Conf., vol. 2, 1993, pp. 832–834, XPOOO617056 p. 832, col. 1, paragraph 7; tables 3–5.

* cited by examiner

Primary Examiner—Floyd D. Higel
(74) Attorney, Agent, or Firm—Barbara V. Maurer

(57) ABSTRACT

The invention relates to an insecticidal and miticidal composition which contains as active ingredients 4-bromo-2-(4-chlorophenyl)-1-(ethoxymethy)-5-(trifluoromethyl)pyrrole-3-carbonitrile in combination with one or more compounds selected from the group consisting of formamidine-type insecticidal and miticidal agents, organosulfur-type insecticidal and miticidal agents, thiocarbamate-type insecticidal and miticidal agents, phenisobromolate, pyrimidifen, milbemectin and dinitromethylheptylphenyl crotonate. The insecticidal and miticidal composition of the invention is effective against pests and mites having resistance to commercial insecticidal and miticidal agents.

19 Claims, No Drawings

INSECTICIDAL OR MITICIDAL COMBINATIONS CONTAINING CHLORFENAPYR

The present Application is a national phase entry of PCT/JP97/04274, filed Nov. 25, 1997, which claims priority of Japanese Application 8/313571, filed Nov. 25, 1996.

FIELD OF THE INVENTION

This invention relates to insecticidal and miticidal compositions which contain as active ingredients 4-bromo-2-(4-chloropheny)-1-(ethoxymethyl)-5-(trifuloromethyl)pyrrole-3-carbonitrile (hereinafter referred to as chlorfenapyr) in combination with a second insecticidal and miticidal ingredient(s) which can be effectively applied especially in the agrohorticultural field.

BACKGROUND OF THE INVENTION

Chlorfenapyr, which is an active ingredient of the insecticidal and miticidal composition of the invention, is known to be effective against insects such as Hemiptera pests such as leafhoppers (Doltocephalidae), Lepidoptera pests such as diamond back moth (*Plutella xylostella*), common cutworm (*Spodoptera litura*) and apple leafminer (*Phyllonorycter ringoniella*) and Thysanoptera pests such as Thrips palmi and yellow tea thrips (*Spirtothrips dorsalis*) and agrohorticultural pests such as mites such as two-spotted spider mite (*Tetranychus urticae koch*), Kanzawa spider mite (*Tetranychus kanzawai kishida*) and *Aculops pelekassi*.

The second active ingredient of the insecticidal and miticidal composition of the invention includes one or more of the following compounds:

1) formamidine-type compounds such as 3-methyl-1,5-bis(2,4-xylyl)-1,3,5-triazapenta-1,4-diene (amitraz), N'-(2-methyl-4-chlorophenyl)-N, N-dimethyl-formamidine hydrochloride (Chlorfenamidine) and the like which are known as effective compounds against agrohorticultural pests such as Hemiptera insects and mites:

2) organosulfur-type compounds such as 2,4,5,4'-tetrachlorodiphenyisulfone (tetradifon), p-chlorophenyl p-chlorobenzenesulfonate (CPCBS) and the like which are known to be effective insecticidal and miticidal agents;

3) thiocarbamate-type compounds such as S-4-phenoxybutyl-dimethylthiocarbamate (fenothiocarb) and the like which are known to be effective against a wide spectrum of agrohorticultural pests;

4) isopropyl 4,4'-dibromobenzilate (fenisobromolate) which is known to be effective against insect and mite pests;

5) 5-chloro-N-{2-[2,3-dimethyl-4-(2-ethoxyethyl) phenoxy]ethyl}-6-ethyl-4-pyrimidinamine (pyrimidifen) which is known to be effective against Hemiptera and Lepidoptera insects and mites;

6) 3:7 mixture of (10E, 14E, 16E, 22Z)-(1R, 4S, 5'S, 6R, 6'R, 8R, 13R, 20R, 21R, 24S)-21, 24-dihydroxy-5', 6',11,13,22-pentamethyl-3,7, 19-trioxatetra-cyclo [15.6.1.1$^{4,8}$. 0$^{20}$, 24]pentacosa-10,14,16,22-tetraene-6-spiro-2'-tetrahydropyran-2-one and (10E, 14E, 16E, 22Z)-(1R, 4S, 5'S, 6R, 6'R, 8R, 13R, 20R, 21R, 24S)-6'-ethyl-21,24-dihydroxy-5', 11,13,22-tetramethyl-3,7, 19-trioxatetra-cyclo[15.6.1.1$^{4,8}$.0$^{20}$,24]pentacosa-10, 14,16,22-tetraene-6-spiro-2'-tetrahydropyran-2-one (milbemectin) which is known to be effective against agrohorticultural mites such as Tetranychidae; and 7) dinitrophenol-type compounds such as dinitromethyl-heptylphenyl crotonate [hereinafter referred to as DPC (Dinocap)] which is known to be effective against agrohorticultural mites such as Tetranychidae and agrohorticultural pathogenic fungi such as powdery mildew.

Although insecticidal and miticidal agents have been developed in order to control various pests such as agrohorticultural pests or hygienic pests and in practice have been used as a single or a mixed agent, pests which have acquired resistance against various agents have been appearing as a result of the repeated use of these agents.

In particular, important economic pests in agrohorticulture such as Tetranychidae, which have a propensity to easily develop resistance against pesticidal agents due to their ability to deposit large numbers of eggs and produce large numbers of generations which, themselves, require only a few days for development are of great concern. Resistance development in this pest family is also favored by a high mutation rate and frequent inbreeding, due to minimal migration. For these reasons, two-spotted spider mite (*Tetranychus urticae koch*), Kanzawa spider mite (*Tetranychus kanzawai kishida*), *Aculops pelekassi*, and the like have acquired resistance, to some degree, against almost all existing pesticidal agents. Therefore, in order to prevent and control the damage caused by Tetranychidae, development of a new insecticidal and miticidal agent which shows a high effect against Tetranychidae which have acquired resistance against the conventional miticidal agents is highly desirable.

However, to obtain an insecticidal and miticidal composition which shows no cross-resistance with existing insecticidal and miticidal agents, has no toxicity problems and has little negative impact on the environment, is extremely difficult. Therefore, a means to delay or prevent the development of resistant strains of pest species is always being sought. In order to apply an effective agent as long as possible, a rotational application of agents with different mechanisms of action is adopted for good pest management practice. However, this approach does not necessarily give satisfactory pest control. Therefore, after a resistance problem has occurred, a countermeasure to resistance by combining insecticidal and miticidal agents has been studied. However, a high synergistic action has not always been found.

Eventhough, chlorfenapyr, is a highly effective miticidal agent at present, it has been recently introduced to the agrochemical market and, in time, may ultimately develop a resistance problem, as has happened with new pesticidal compounds so often in the past.

Therefore, it is an object of this invention to provide an insecticidal and miticidal composition which demonstrates a high controlling effect even against Tetranychidae which have acquired resistance against chlorfenapyr.

SUMMARY OF THE INVENTION

In order to establish a countermeasure to a resistance problem in Tetrachychidae against chlorfenapyr before such a problem occurs, the synergistic action with the existing insecticidal, miticidal and fungicidal agents was studied using resistant species which have been artificially established in the laboratory by selecting Tetrachychidae which have been treated with chlorfenapyr. Thus, it has now been found that an insecticidal and miticidal composition which contains as active ingredients chlorfenapyr in combination with one or more compounds specified in a select group of insecticidal and miticidal ingredients shows a joint action or synergistic effect which could not be foreseen from each individual ingredient alone. Namely, the invention exists in the insecticidal and miticidal composition which contains as active ingredients chlorfenapyr in combination with one or more compounds selected from the group consisting of formamidine-type insecticidal and miticidal agents, organosulfur-type insecticidal and miticidal agents, thiocarbamate-type insecticidal and miticidal agents, phenisobromolate, pyrimidifen, milbemectin and dinitromethylheptylphenyl crotonate (hereinafter referred to as Group A).

DETAILED DESCRIPTION OF THE INVENTION

Chlorfenapyr, which is an active ingredient of the insecticidal and miticidal composition of the invention, is a known compound (Japanese Laid-open (Kokai) Patent Publication No. 104042/89). Compounds which are suitable for use as the second active ingredient in the composition of the invention such as one or more of the following compounds:

1) formamidine-type compounds, preferably amitraz end chlorphenamidine:
2) organosulfur-type compounds, preferably tetradifon and p-chlorophenyl p-chlorobenzenesulfonate;
3) thiocarbamate-type compounds, preferably fenothiocarb;
4) fenisobromolate;
5) pyrimidifen;
6) milbemectin and
7) dinitromethylheptylphenyl crotonate are all known compounds and are commercial products which are readily available.

For the preparation of the insecticidal and miticidal composition of the invention, it is suitable to formulate as a wettable powder, aqueous concentrate, emulsion, liquid concentrate, sol (flowable agent), powder, aerosol, or the like, by conventional methods such as admixing chlorfenapyr and one or more compounds of Group A with a suitable carrier and auxiliaries, such as emulsifiers, dispersants, stabilizers, suspending agents, penetrants, and the like.

The content of the total active ingredients of the composition of the invention, expressed as weight/weight %, is preferably in the range of about 1–90% for wettable powder, aqueous concentrate, emulsion, liquid concentrate and sol formulations. The preferable content of total active ingredients is about 0.5–10% for powder formulations and about 0.01–2% for aerosol formulations.

Carriers suitable for use in the insecticidal and miticidal compositions of the invention may be any solid or liquid carrier which is commonly used for an agrohorticultural composition. Various surfactants, stabilizers and other auxiliary ingredients may be used according to the necessity. In commercially useful formulations, the composition of the invention may also be present in a mixture with other active agents, for example various insecticidal, miticidal, fungicidal and herbicidal agents, plant growth regulators, repellants, attractants, synergists and fertilizers and fragrances, in order to expand its applicability.

The ratio of chlorfenapyr to the compound(s) of Group A in the insecticidal and miticidal composition of the invention is about 1 weight part of chlorfenapyr to about 0.01–100 weight parts, preferably about 0.1–20 weight parts, of a compound(s) of Group A.

The insecticidal and miticidal composition of the invention is particularly effective for the control of Tetranychidae such as two-spotted spider mite (*Tetranychus urticae koch*), *Tetranychus cinnabarinus* (boisduyal), Kanzawa spider mite (*Tetranychus Kanzawai kishida*), *Tetranichus viennensis zacher*, and the like.

Advantageously, the insecticidal and miticidal composition of the invention shows not only a synergistic miticidal effect against the above-mentioned Tetranychidae, but also demonstrates simultaneous control of troublesome pests such as leafroller moths (Tortricidae), Carposinidae, leafminer moths (Lyonetiidae), plant bugs (Pentatomidae), aphids (Aphididae), leaf-hoppers (Deltociphalidae), thrips (Thripidae), diamond back moths (*Plutella xylostella*), *Mamestra brassicae*, leaf beetles (Chrysomelidae), whiteflies (Aleyrodidae) and the like on important agronomic crops such as fruit trees, for example citrus, apple and pear; tea plants; vegetables and the like.

Although the application amount of the composition of the invention may differ according to prevailing conditions such as the population density, the kinds and cultivation form of the target crop the weather conditions, the manner of application, and the like, in general, the total amount of chlorfenapyr in combination with the compound(s) of Group A is about 0.1–1,000 g, preferably about 40–500 g, per 10 ares. In actual practice, the composition of the invention when in the form of a wettable powder, aqueous concentrate, emulsion, liquid concentrate, sol, or the like may be diluted with water and applied to the crop at an application rate of about 100–700 liters per 10 ares. When the inventive composition is formulated as a powder or aerosol, the crop may be treated with the undiluted formulation.

The insecticidal and miticidal composition of the invention is further illustrated in the examples set forth hereinbelow These examples are not intended to limit the scope of the invention. All parts are parts by weight.

EXAMPLE 1
FORMULATION EXAMPLE 1 EMULSION

| | |
|---|---|
| Clorfenapyr | 10 parts |
| Amitraz | 30 parts |
| Xylene | 25 parts |
| Dimethyl formamide | 20 parts |
| Sorpol 3005X | 15 parts |

(Polyoxyethylene type surfactant manufactured by Toho Chemical Industry Co., Ltd., commercial name)

An emulsion is obtained by mixing homogneously and dissolving the above-mentioned ingredients.

EXAMPLE 2
FORMULATION EXAMPLE 2 WETTABLE POWDER

| | |
|---|---|
| Chlorfenapyr | 10 parts |
| Tetradifon | 10 parts |
| Carplex #80 | 20 parts |

(White carbon manufactured by Shionogi & Co., Ltd, commercial name)

| | |
|---|---|
| Zeeklite SP | 52 parts |

(Mixture of kaolinite and cericite manufactured-by Zeeklite Ind., commercial name)

| | |
|---|---|
| Calcium ligninsulfonate | 8 parts |

A wettable powder is obtained by homogeneously mixing the above-mentioned ingredients by jet air mill.

EXAMPLE 3
FORMULATION EXAMPLE 3 SOL (FLOWABLE AGENT)

| | |
|---|---|
| Chlorfenapyr | 5 parts |
| Fenothiocarb | 25 parts |
| Ethylene glycol | 8 parts |
| Sorpol AC3020 | 5 parts |

| | |
|---|---|
| Xanthan gum | 0.1 parts |
| Water | 56.9 parts |

Chlorfenapyr, fenothiocarb and a previously prepared mixture of ethylene glycol, Sorpol AC3020 and xanthan gum are well mixed in water and dispersed. This slurry is then wet pulverized by Dynomill (Shinmaru Enterprises) to obtain a sol (flowable agent).

Each of the above-prepared formulations is suitable to be used as an agrochemical.

EXAMPLE 4
TEST EXAMPLE I

In this experiment, the miticidal effect against female imagines (adults) of Kanzawa spider mite (*Tetranychus kanzawai kishida*) which are registrant to chlorfenapyr is evaluated.

Round leaf disks (2 cm diameter) are cut out of a first leaf of kidney bean by a leaf punch and 4 sheets of the disks are placed on wet sanitary cotton in a plastic cup (8 cm diameter). On each leaf disk, 4 female imagines of Kanzawa spider mite (*Tetranychus kanzawai kishida*) which had acquired a strong resistance to chlorfenapyr are inoculated.

After the inoculation, chlorfenapyr and a compound(s) selected from group A are dispersed in water containing 200 ppm of an extender (Sorpol 3005X) and diluted such that a predetermined concentration of active ingredient is obtained. Each plastic cup is sprayed with 3.5 ml of a test solution with a rotary spray tower (Mizuho Scientific Co., Ltd.) and stored in a constant temperature chamber held at 25±1° C. (32 individuals are tested per concentration, 4–5 concentrations are evaluated per formulation, and 2 performances were repeated). Two days after treatment, the number of living and dead female imagines of Kanzawa spider mite (*Tetranychus kanzawai kishida*) which had acquired a strong resistance to chlorfenapyr is counted and the mortality (%) is calculated according the formula shown hereinbelow.

Mortality (%)=

$$\text{Mortality (\%)} = \frac{\text{Number of dead mite}}{\text{Number of alived mite} + \text{Number of dead mite}} \times 100$$

Using these data, the $LC_{50}$ values are obtained by conventional probit analysis techniques. A co-toxicity coefficient is calculated by applying Sun and Johnson's formula (J. Econ. Ent., Vol 53, p. 887, 1980) which is generally used to determine the degree of synergistic activity.

The $LC_{50}$ value of each individual effective ingredient which constitutes the insecticidal and miticidal composition of the invention is shown in Table I. The $LC_{50}$ values and the co-toxicity coefficients of the composition of the invention are shown in Table II.

Co-toxicity coefficient=$T^c$ $$T^c = \frac{\text{Actual toxicity index of mixture}}{\text{Theoretical toxicity index of mixture}} \times 100$$

For $T^c$ values greater than 100, the greater value indicates a stronger synergistic action. For a $T^c$ value equal to 100, an additive action is indicated. For $T^c$ values less than 100, the lesser value indicates a greater antagonistic action. A more detailed description of the calculation of the co-toxicity coefficient using the above-referenced Sun and Johnson formula follows.

The $LC_{50}$ values of Test Compound A alone and Test Compound B alone and the $LC_{50}$ value of the (A+B) mixture M is determined.

Actual toxicity index of mixture M=$M^{ti}$

Each $LC_{50}$ value of effective ingredient A and effective ingredient B and the $LC_{50}$ value of the mixture of A+B are used to determine the actual toxicity index as shown in the equation below.

$$M^{ti} = \frac{LC_{50} \text{ of } A}{LC_{50} \text{ of } M} \times 100$$

Theoretical toxicity index of mixture M=Th.$M^{ti}$

Th.$M^{ti}$=(Toxicity index of A×%A in M+Toxicity index of B×%B in M)

Toxicity index of B=$B^{ti}$ $$B^{ti} = \frac{LC_{50} \text{ of } A}{LC_{50} \text{ of } B} \times 100$$

Toxicity index of A=$A^{ti}$
$A^{ti}$=100

TABLE I

Evaluation Of The Effect Of Test Compounds Against Female Imago Of Kanzawa Spider Mite Which Have Acquired Resistance Against Chlorfenapyr

| TEST COMPOUND | $LC_{50}$ (ppm) |
|---|---|
| Chlorfenapyr | 1500 |
| Amitraz | 200 |
| Tetradifon | 4900 |
| Kelthane (Dicofol) | 32 |
| Phenisobromalate* | 280 |
| Fenothiocarb | 1000 |
| Pyrimidifen | 10 |
| Avermectins | 0.13 |
| Milbemectin | 0.28 |
| Binapacryl[a] | 180 |
| DPC | 630 |

*2,4-dinitro-6-sec-butylphenyldimethyl-acrylate

By comparison, the $LC_{50}$ value for chlorfenapyr against a susceptible strain of Kanzawa spider mite is about 5 ppm.

As can be seen from the data on Table I, the resistant strain of Kanzawa spider mite which was obtained by a long artificial selection procedure against chlorfenapyr in a laboratory on a colony of Kanzawa spider mite which had been collected in the field, has developed about a 300-fold resistance to chlorfenapyr.

In the case of amitraz, phenisobromolate, Binapacryl and DPC, this Kanzawa spider mite is thought to originate from a colony which had acquired resistance to these insecticidal and miticidal agents prior to the time of collection in the field. These compounds all showed low effects.

The test compounds: Kelthane (dicofol), pyrimidifen, avermectins and milbemectin all demonstrate a high miticidal effect in this experiment.

The test compounds tetradifon and fenothiocarb demonstrate a low miticidal effect in this experiment.

TABLE II

Evaluation Of The Effect Of Test Mixtures Against Female Imago Of Kanzawa Spider Mite Which Have Acquired Resistance Against Chlorfenapyr

| TEST MIXTURE | RATIO[1] | LC$_{50}$ ppm) | T$^C$ |
|---|---|---|---|
| Chlorfenapyr + Amitraz | 1:5 | 64 | 370 |
| Chlorfenapyr + Tetradifon | 1:3.2 | 72 | 4400 |
| Chlorfenapyr + Kelthane | 1:5.3 | 34 | 110 |
| Chlorfenapyr + Phenisobromolate | 1:6 | 97 | 330 |
| Chlorfenapyr + Fenothiocarb | 1:10 | 270 | 380 |
| Chlorfenapyr + Pyrimidifen | 4:5 | 4.0 | 450 |
| Chlorfenapyr + Avermectins | 5:1 | 0.56 | 140 |
| Chlorfenapyr + Milbemectin | 5:1 | 0.75 | 220 |
| Chlorfenapyr + Binapacryl | 1:10 | 150 | 130 |
| Chlorfenapyr + DPC | 5:12 | 140 | 540 |

[1]Chlorfenapyr:Second active Ingredient
T$^C$ = Co-toxicity Coefficient

As can be seen from the data on Table II, the co-toxicity coefficient of each of the test mixtures containing chlorfenapyr in combination with either amitraz or tetradifon or phenisobromolate or fenothiocarb or pyrimidifen or milbemectin or DPC is a value significantly greater than 100, which is indicative of strong synergistic action.

What is claimed is:

1. An insecticidal or miticidal composition which contains as active ingredients synergistic amounts of present in a ratio of about 1 weight part chlorfenapyr to about 0.01–100 total weight parts of one or more compounds selected from the group consisting of formamidine insecticidal or miticidal compounds, organosulfur insecticidal or miticidal compounds, thiocarbamate insecticidal or miticidal compounds, phenisobromolate, pyrimidifen, milbemectin and dinitromethylheptylphenyl crotonate.

2. The composition according to claim 1 wherein the active ingredients comprise chlorfenapyr in combination with one or more formamidine compounds.

3. The composition according to claim 2 wherein the formamidine compound is amitraz or chlorphenamidine.

4. The composition according to claim 1 wherein the active ingredients comprise chlorfenapyr in combination with one or more organosulfur compounds.

5. The composition according to claim 4 wherein the organosulfur compound is tetradifon or p-chlorophenyl p-chlorobenzenesulfonate.

6. The composition according to claim 1 wherein the active ingredients comprise chlorfenapyr in combination with one or more thiocarbamate compounds.

7. The composition according to claim 6 wherein the thiocarbamate compound is fenothiocarb.

8. The composition according to claim 1 wherein the active ingredients comprise chlorfenapyr in combination with one or more compounds selected from the group consisting of phenisobromolate, pyrimidifen, milbemectin and dinitromethylheptylphenyl crotonate.

9. The composition according to claim 1 wherein the chlorfenapyr is present in a ratio of about 1 weight part to about 0.01–100 total weight parts of one or more compounds selected from the group consisting of amitraz, chlorphenamidine, tetradifon, p-chlorophenyl p-chlorobenzenesulfonate, fenothiocarb, phenisobromolate, pyrimidifen, milbemectin and dinitromethylheptylpheny crotonate.

10. A process for the preparation of a composition of claim 1 which comprises admixing the active ingredients with an agrohorticulturally acceptable solid or liquid carrier.

11. A method of controlling insecticidal o miticidal pests which have acquired resistance to 4-bromo-2-(4-chlorophenyl)-1-(ethoxymethyl)-5-(trifluoromethyl) pyrrole-3-carbonitril at a locus which comprises applying to the locus an effective amount of about 0.1–1000 grams per 10 acres of an insecticidal and miticidal composition comprising as active ingredients synergistic amounts of about 1 weight part of 4-bromo-2-(4-chlorophenyl)-1-(ethoxymethyl)-5-(trifluoromethyl) pyrrole-3-carbonitrile to about 0.01–100 total weight parts of one or more compounds selected from the group consisting of formamidine insecticidal or miticidal compounds, organosulfur insecticidal or miticidal compounds, thiocarbamate insecticidal or miticidal compounds, phenisobromolate, pyrimidifen, milbemectin and dinitromethylheptylphenyl crotonate.

12. A method according to claim 11 wherein the active ingredients of the composition comprise chlorfenapyr in combination with one or more formamidine insecticidal or miticidal compounds.

13. A method according to claim 12 wherein the formamidine insecticidal compound is amitraz or chlorphenamidine.

14. A method according to claim 11 wherein the active ingredients comprise chlorfenapyr in combination with one or more organosulfur compounds.

15. A method according to claim 14 wherein the organosulfur compound is tetradifon or p-chlorophenyl p-chlorobenzenesulfonate.

16. A method according to claim 11 wherein the active ingredients comprise chlorfenapyr in combination with one or more thiocarbamate compounds.

17. A method according to claim 16 wherein the thiocarbamate compound is fenothiocarb.

18. A method according to claim 11 wherein the active ingredients of the composition comprise chlorfenapyr in combination with one or more compounds selected from the group consisting of phenisobromolate, pyrimdifen, milbemectin and dinitromethylheptylphenyl crotonate.

19. A method according to claim 11 wherein the chlorfenapyr is present in the composition in a ratio of a bout 1 weight part to about 0.01–100 total weight parts of one or more compounds selected from the group consisting of amitraz, chlorphenamidine, tetradifon, p-chlorophenyl p-chlorobenzenesulfonate, fenothiocarb, phenisobromolate, pyrimidifen, milbemectin and dinitromethylheptylphenyl crotonate.

* * * * *